(12) United States Patent
Schnall

(10) Patent No.: US 7,621,877 B2
(45) Date of Patent: Nov. 24, 2009

(54) BODY SURFACE PROBE, APPARATUS AND METHOD FOR NON-INVASIVELY DETECTING MEDICAL CONDITIONS

(75) Inventor: Robert P. Schnall, Bialik (IL)

(73) Assignee: Itamar Medical Ltd., Caesarea (IL)

( * ) Notice: Subject to any disclaimer, the term of this patent is extended or adjusted under 35 U.S.C. 154(b) by 63 days.

(21) Appl. No.: 10/520,273

(22) PCT Filed: Jul. 15, 2003

(86) PCT No.: PCT/IL03/00586

§ 371 (c)(1),
(2), (4) Date: Jan. 18, 2005

(87) PCT Pub. No.: WO2004/006748

PCT Pub. Date: Jan. 22, 2004

(65) Prior Publication Data

US 2006/0064024 A1 Mar. 23, 2006

Related U.S. Application Data

(60) Provisional application No. 60/395,613, filed on Jul. 15, 2002.

(51) Int. Cl.
*A61B 5/02* (2006.01)
(52) U.S. Cl. ........................ 600/507; 600/481; 600/500; 600/504
(58) Field of Classification Search .................. 600/300, 600/301, 481, 483, 485, 484, 500, 504, 506, 600/507; 606/201
See application file for complete search history.

(56) References Cited

U.S. PATENT DOCUMENTS 3,412,729 A * 11/1968 Smith, Jr. ..................... 600/324

(Continued)

FOREIGN PATENT DOCUMENTS

IL 97/00249 * 2/1998

(Continued)

*Primary Examiner*—Patricia C Mallari

(57) ABSTRACT

A probe for application to a selected area of a subject's skin covering a body part, which selected area serves as a measurement site for measuring changes in the pulsatile arterial blood volume thereat, includes: a base for application to the selected area of the subject's skin at the measurement site; a pressure applicator for applying a static pressure to the subject's skin at the measurement site; and a sensor for sensing changes in the pulsatile arterial blood volume at the measurement site. The pressure applicator is designed to apply to the measurement site a static pressure of a magnitude to partially unload the wall tension of, but not to occlude, the arteries. The pressure applicator is configured to substantially prevent venous distention and blood pooling at the measurement site by permitting free venous drainage through tissues surrounding the measurement site. This is done by configuring the pressure applicator to apply the static pressure to a relatively restricted area of the subject's skin, which area occupies a relatively small fraction of the surface perimeter of the respective body part at the measurement site, to thereby permit free venous drainage from the measurement site via a wide region of unrestricted passageways surrounding the measurement site.

54 Claims, 10 Drawing Sheets

U.S. PATENT DOCUMENTS

| | | | |
|---|---|---|---|
| 4,164,937 A * | 8/1979 | Spencer | 600/479 |
| 4,807,638 A * | 2/1989 | Sramek | 600/485 |
| 4,896,676 A * | 1/1990 | Sasaki | 600/494 |
| 5,230,342 A * | 7/1993 | Bobo et al. | 600/490 |
| 5,238,000 A * | 8/1993 | Niwa | 600/502 |
| 5,368,039 A * | 11/1994 | Moses | 600/494 |
| 5,640,964 A * | 6/1997 | Archibald et al. | 600/490 |
| 5,743,856 A * | 4/1998 | Oka et al. | 600/493 |
| 6,132,382 A * | 10/2000 | Archibald et al. | 600/485 |
| 6,162,181 A * | 12/2000 | Hynson et al. | 600/485 |
| 6,319,205 B1 | 11/2001 | Goor et al. | |
| 6,322,515 B1 * | 11/2001 | Goor et al. | 600/485 |
| 6,332,869 B1 * | 12/2001 | Ogura et al. | 600/490 |
| 6,461,305 B1 | 10/2002 | Schnall | |
| 6,516,289 B2 * | 2/2003 | David | 600/384 |
| 6,749,567 B2 * | 6/2004 | Davis et al. | 600/300 |
| 2001/0003792 A1 * | 6/2001 | Ogura et al. | 600/500 |
| 2002/0026121 A1 * | 2/2002 | Kan | 600/500 |
| 2002/0072681 A1 | 6/2002 | Schnall | |
| 2002/0188206 A1 * | 12/2002 | Davis et al. | 600/485 |
| 2003/0109772 A1 * | 6/2003 | Mills | 600/310 |

FOREIGN PATENT DOCUMENTS

IL          99/00292        * 12/1999

* cited by examiner

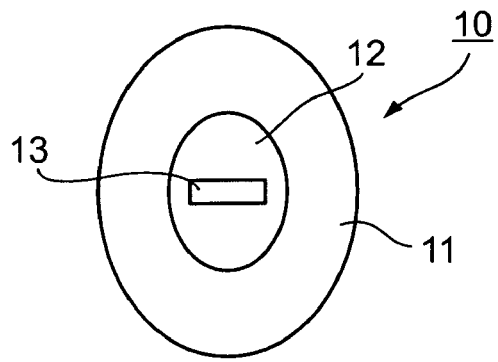
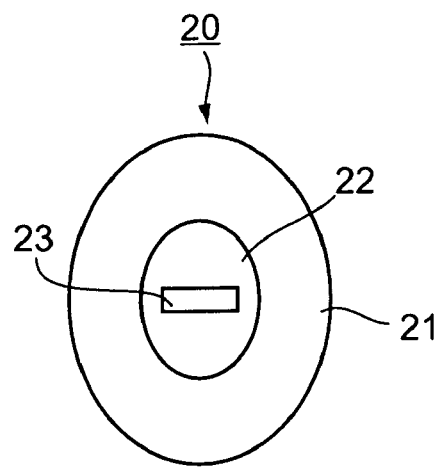
Fig. 1a Fig. 2a
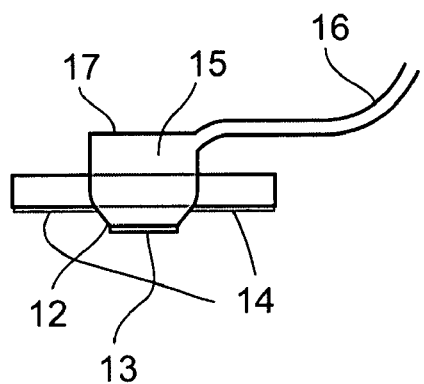
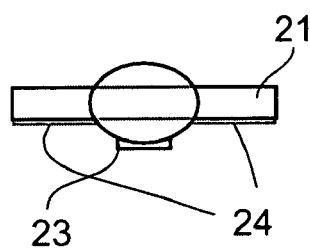
Fig. 1b Fig. 2b
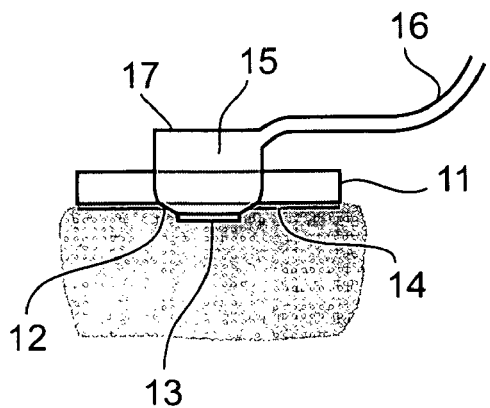
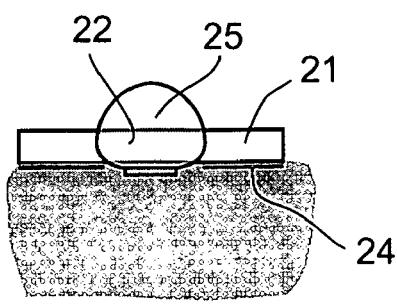
Fig. 1c Fig. 2c

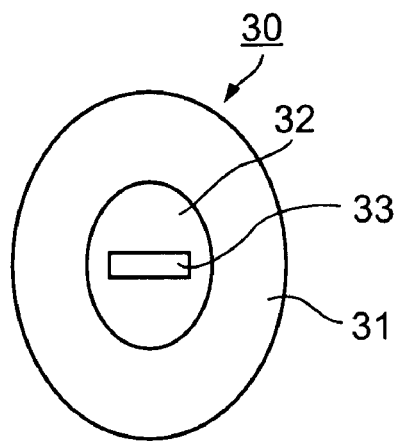
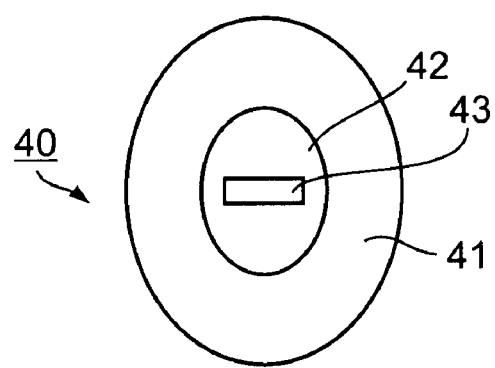
Fig. 3a    Fig. 4a
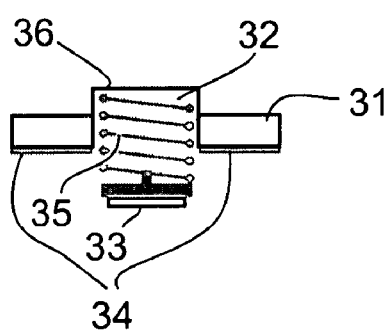
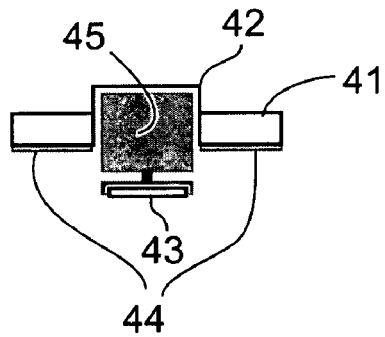
Fig. 3b    Fig. 4b
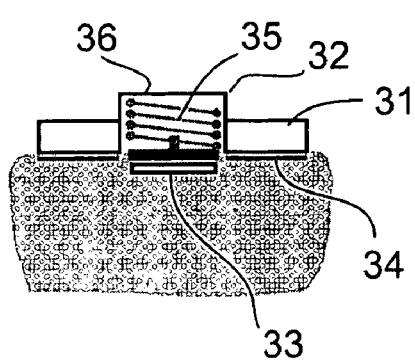
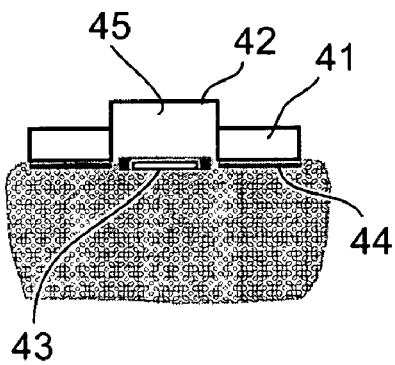
Fig. 3c    Fig. 4c

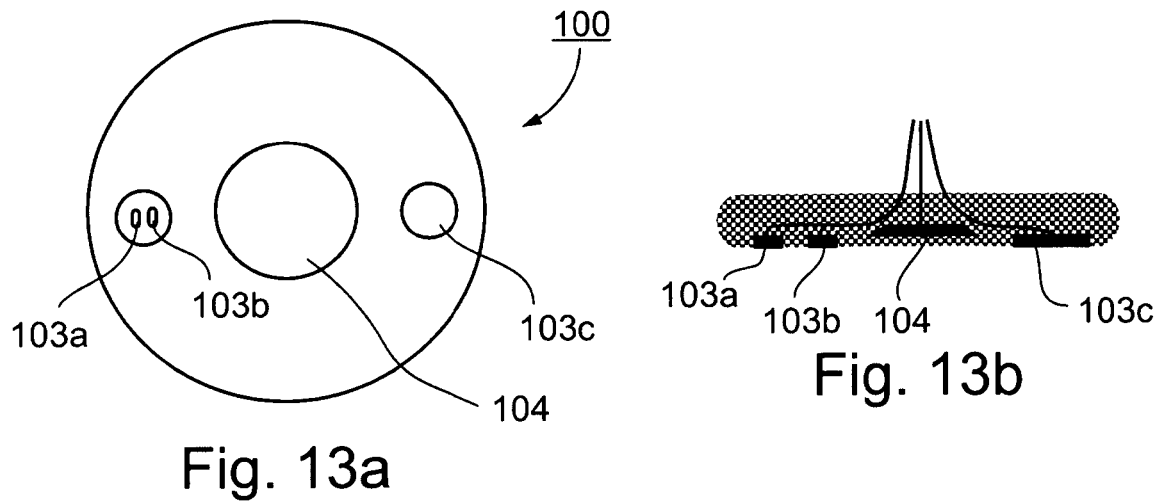
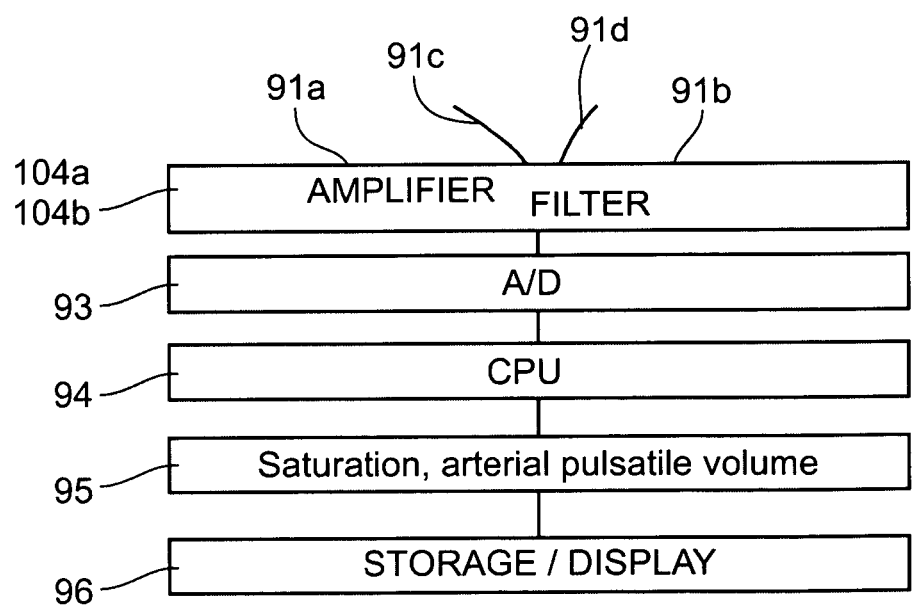

30 sec

BODY SURFACE PROBE, APPARATUS AND METHOD FOR NON-INVASIVELY DETECTING MEDICAL CONDITIONS

RELATED PATENT APPLICATION

This application is a National Phase Application of PCT/IL03/00586 having International Filing Date of 15 Jul. 2003 which claims priority from U.S. Provisional Patent Application No. 60/395,613 filed 15 Jul. 2002.

FIELD AND BACKGROUND OF THE INVENTION

The present invention relates to probes for application to selected areas of a subject's body for monitoring the physiological condition or changes thereof of a mammalian subject or detecting various medical conditions of the subject. The invention also relates to apparatus utilizing such probes, and also to methods utilizing such probes for detecting various medical conditions or physiological states.

The invention is particularly useful for the non-invasive detection of a medical condition or physiological state of a subject by monitoring changes in the peripheral arterial tone as described in U.S. Pat. Nos. 6,319,205, 6,322,515, 6,461,305 and 6,488,633, the contents of which are incorporated herein by reference, and in corresponding patents and applications filed in other countries, hereinafter referred to as the above-identified patents and applications. The invention is therefore described below with respect to the above-identified patents and applications, but it will be appreciated that various features of the invention could also be advantageously used in other probes and in the detection of other types of medical conditions or physiological conditions.

The above-identified patents and applications disclose various probe constructions, methods and apparatus for the non-invasive detection of a medical condition or physiological state of a subject, particularly by monitoring changes in the peripheral arterial tone as manifested by changes in the pulsatile arterial blood volume in a terminal extremity of a body part, e.g., a digit (finger or toe) of the subject. The various medical conditions detected by such probes, as described therein, include myocardial ischemia, sleep apnea and other sleep disordered breathing conditions, endothelial dysfunction (ED), and sleep disorders, as well as certain physiological states, such as mental stress, sympathetic nervous system reactivity, blood pressure, REM stage sleep, responses to physical, pharmacological or mental agents or stressors, etc.

In general, the probes described in the above-identified patents and applications include a housing defining at least one compartment for receiving the distal end of the subject's body part (e.g., a finger or toe), including its terminal-most extremity, such that the compartment is closed at one end and open at the opposite end, and a sensor for sensing a predetermined condition of the body part after received within the compartment. The preferred embodiments described therein are particularly useful for monitoring peripheral arterial tone in a subject's finger or toes, and for that purpose, they included pressurizing means for applying a static pressure field substantially uniformly around the distal end of the subject's finger, including its terminal-most extremity. The pressure field is of a predetermined magnitude sufficient to substantially prevent distention of the venous vasculature, to substantially prevent venous blood pooling within the applied pressure field, to substantially prevent uncontrolled venous backflow and retrogade shockwave propagation into the distal end of the finger, and to partially unload the wall tension of, but not to occlude, the arteries in the distal end of the finger when at heart level or below.

The prevention of venous pooling and venous distention is intended to prevent the occurrence of induced veno-arteriolar reflex vasoconstriction. The prevention of uncontrolled venous backflow and retrogade shockwave propagation into the distal end of the finger, and the partial unloading of arterial wall tension, contribute to the optimal measurement of arterial pulse signals divorced from venous volume changes and divorced from confounding induced reflex changes due to artifacts of the measurement method. The probe sensors described in the above-identified patents and applications were thus optimally configured to sense changes in the distal end of the subject's finger (or other body part) related to changes in volume therein due to pulsatile changes in instantaneous blood volume related to arterial tone.

It would be highly desirable to provide a probe allowing measurements to be made at a broader range of body sites. Such a probe could be used to facilitate the non-invasive determination of a wide range of physiological conditions, e.g., by comparing physiological changes at sites at which peripheral arterial tone are known to be governed by differing physiological control mechanisms. Such knowledge can, for example, allow for the discrimination between reflex mediated arterial tone changes and changes in arterial pulsatile amplitude due to mechanical hemodynamic consequences of reduced or otherwise changed cardiac stroke volume.

In addition to the advantages conferred by facilitating the measuring of peripheral arterial tone at a broader range of body sites, the ability to record a pulsatile arterial signal that is effectively divorced from venous blood changes, provides important advantages for the non-invasive measurement of blood oxygen saturation by the method of pulse oximetry. An important case in point is the application of such a probe to a measurement site overlying a superficial artery, wherein the level of blood oxygen may more accurately represent the actual systemic arterial oxygenation level than would measurements derived from sites overlying a vascular bed comprised largely of microvascular arterial and venous blood vessels. The combined, simultaneous, measurement of arterial blood saturation level and peripheral arterial pulsatile volume changes from the same probe would provide even greater diagnostic advantages.

Moreover, such a probe could be used at body locations better tolerated by the subject, or less likely to result in the subject removing the device, as is the case for a finger mounted probe, for example. Such a probe would also be useful for measurements on babies, young children, mentally compromised subjects, or subjects with structural or functional disorders of the fingers or toes.

OBJECTS AND BRIEF SUMMARY OF THE INVENTION

An object of the present invention is to provide a probe which allows measurements to be made at virtually any body site and thereby provides many of the advantages discussed above. Another object of the invention is to provide apparatus for use with such probes; and a further object is to provide a method of using such probes for detecting various medical conditions or physiological states.

According to one aspect of the present invention, there is provided a probe for application to a selected area of a subject's skin covering a body part, which selected area serves as a measurement site for measuring changes in the pulsatile arterial blood volume thereat, comprising: a base for application to the selected area of the subject's skin at the measurement site; a pressure applicator carried by the base for applying a static pressure to the subject's skin at the measurement site when the base is applied thereto; and a sensor carried by the pressure applicator for sensing changes in the pulsatile arterial blood volume at the measurement site when the base is applied thereto; the pressure applicator being designed to apply to the measurement site, when the base is applied thereto, a static pressure of a sufficient magnitude to partially unload the wall tension of, but not to occlude, arterial blood vessels at the measurement site; the pressure applicator being configured to substantially prevent venous distention and blood pooling at the measurement site by applying sufficient external counter pressure to effectively collapse the underlying veins and limit the local venous blood flow to the arterial throughput while permitting free venous drainage with respect to the measurement site through tissues surrounding the measurement site.

According to further features of the invention described below, the probe is configured to be applied to a relatively restricted area of the subject's skin to apply the static pressure to said relatively restricted area, which area does not completely encircle the respective body part at the measurement site; the pressure applicator occupying a relatively small fraction of the surface perimeter of the respective body part at the measurement site, to thereby permit free venous drainage from the measurement site via a wide region of unrestricted passageways surrounding the measurement site.

Preferably, the pressure applicator applies to the measurement site a static pressure which is above the subject's local venous pressure and slightly below the subject's diastolic blood pressure.

Several embodiments of the invention are described below for purposes of example. In one embodiment, the pressure applicator comprises a fluid chamber and an external source of fluid for applying the pressure to the measurement site and subsequently measuring the pressure. In another embodiment, the pressure applicator comprises a fluid chamber with at least one elastic wall constructed to utilize Laplace's law and including a self-contained fluid for applying the static pressure to the measurement site such that the level of pressure applied by the probe is substantially unaffected by the mechanical characteristics of the underlying tissues. In a further embodiment, the pressure applicator comprises a chamber including a spring therein for applying the static pressure to the measurement site; and in a still further embodiment, the pressure applicator comprises a resilient elastomeric material, such as sponge rubber or the like, for applying the static pressure to the measurement site.

According to another aspect of the present invention, there is provided apparatus for detecting and indicating a medical condition of a subject, comprising: a probe as set forth above for application to a measurement site on the subject's skin and for producing an output corresponding to measured changes in the pulsatile arterial blood volume thereat; and a data processor system for utilizing the measured changes to detect and indicate a medical condition or a physiological state of the subject.

According to further features in some described embodiments, the apparatus further comprises at least one additional probe as set forth above for application to at least one additional measurement site on the subject's skin and for measuring changes in the pulsatile arterial blood volume thereat; the data processor system utilizing the measured changes of both of the probes for detecting and indicating the medical condition or physiological state of the subject.

As will be described more particularly below, such probes may be constructed for application to measurement sites in which the vascular beds thereat have different levels of autonomic nervous system activity; or in which the vascular beds are mainly comprised of conduit or conducting arteries; or in which the pulsatile volume of the vascular beds are respectively predominantly affected by autonomic nervous system activity and by the level of systemic blood pressure, etc.

According to a further described preferred embodiment, the probe could include an electrode for sensing a bio-potential such as the electrocardiograph (ECG) signal of a subject, the data processor utilizing the measured changes in the pulsatile arterial blood volume, and the ECG signal, to determine the pulse transit time (PTT) or the pulse propagation velocity. Sensors of other physiological parameters could also be substituted for the bio-potential sensor. As will be described more particularly below, such information can also be extremely useful in detecting and indicating the medical condition of the subject.

According to still further aspects of the present invention, there is provided a method and apparatus using probes as set forth above for detecting and indicating various medical conditions of a subject.

Comparison with Finger (and Toe) Probes

Heretofore, the practical application of the arterial pulse signal measurement methodology for isolating an essentially pure arterial pulsatile volume measurement has been restricted to sites which incorporated the body's terminal extremities, i.e., a finger or toe. This is due to the fact that such probes are applied circumferentially over the entire perimeter of the body region being measured in order to apply to the measurement site the required static pressure which partially unloads the wall tension of, but does not occlude, the arteries in the measurement site. Thus, a full perimeter pressure band inherently induces venous distention and venous pooling distal to the site of pressure application.

Such venous distention and venous pooling can only be prevented if the entire distal surface of the measurement site, up to and including the very tip, is enclosed within the uniform pressure field such that no part of the vascular bed is in fact distal to the pressure field. The probes described in the above cited patents and applications were generally constructed to ensure that the applied pressure field reaches up to, and in fact beyond, the terminal end of the extremity so as to avoid the occurrence of venous pooling and venous distention, and thus avoid the disadvantageous consequences of unchecked distal venous pooling and distention.

In contrast, the probes constructed in accordance with the present invention are able to measure arterial pulse signals and their changes from virtually any point on the body surface without causing deleterious venous-pooling effects. This is achieved by constructing the probes to apply the appropriate pressure field to a given body surface without completely encircling the body part at the measurement site. Under such circumstances distal venous pooling is avoided since venous drainage can occur freely via alternate, fully unrestricted pathways surrounding the point or region of measurement and thus the need to apply a pressure field extending distally to the terminal end of the extremity is avoided. At the actual site of the measurement, the applied pressure would be such that the veins would be maintained in a collapsed state save for the transmitted pulsatile arterial throughput.

Furthermore, an expanded region of uniform pressure application, extending in area beyond the central measurement region, confers the additional benefits of extending the effective boundary of the pressure field overlying the sensing region, and in addition, of buffering the measurement site from retrograde venous shockwave signals and the like.

In addition, since such probes can be constructed for application to virtually any body site, such probes allow measurements to be concurrently made, as indicated above and as will be described more particularly below, at a plurality of different body sites to provide considerable additional information useful for indicating or detecting various medical conditions or physiological states of the subject.

Further features and advantages of the invention will be apparent from the description below.

BRIEF DESCRIPTION OF THE DRAWINGS

The invention is herein described, by way of example only, with reference to the accompanying drawings, wherein:

FIGS. 1a and 1b are diagrammatic top and side views, respectively, illustrating one form of probe constructed in accordance with the present invention in which the pressure applicator includes a fluid chamber having an external source of fluid for facilitating pressure application and for measuring changes in the pulsatile arterial blood volume; and FIG. 1c is a view corresponding to that of FIG. 1b showing the probe applied to a subject's skin for measuring changes in the pulsatile arterial blood volume thereat;

FIGS. 2a, 2b and 2c are diagrammatic views corresponding to FIGS. 1a, 1b and 1c, respectively, illustrating another probe constructed in accordance with the present invention in which the pressure is applied by a fluid chamber having at least one elastic wall constructed to utilize Laplace's law, as more particularly described for example in published Application U.S. 2002/0072681 A1;

FIGS. 3a, 3b and 3c are diagrammatic views corresponding to those of FIGS. 1a, 1b and 1c, respectively, illustrating a third probe constructed in accordance with the present invention in which the pressure applicator includes a spring for applying the static pressure;

FIGS. 4a, 4b and 4c are diagrammatic views, corresponding to FIGS. 1a, 1b and 1c, respectively, illustrating a fourth probe constructed in accordance with the present invention in which the pressure applicator includes a resilient sponge material for applying the static pressure;

FIGS. 11a, 11b and 11c are diagrammatic views, corresponding to FIGS. 1a, 1b and 1c, respectively, illustrating a further probe constructed in accordance with the present invention including an optical sensor; while

FIGS. 13a and 13b are plan and side views, respectively, corresponding to FIGS. 11d and 11e, respectively, but illustrating the probe as also including an ECG electrode;

FIG. 14 is a block diagram illustrating apparatus constructed in accordance with the present invention to utilize the measurements of the probe of FIGS. 13a and 13b;

Figure 5A:
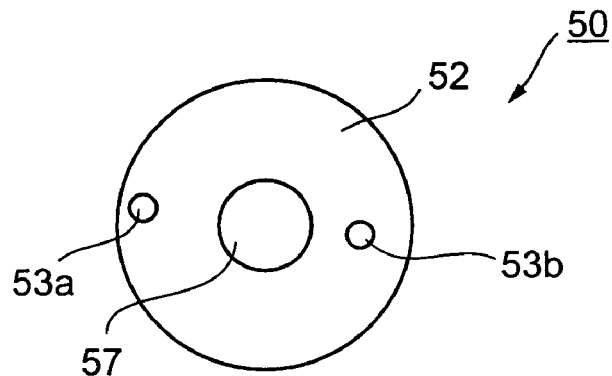
FIGS. 5a, 5b and 5c are diagrammatic views, corresponding to those of FIGS. 4a, 4b and 4c, more particularly illustrating the structure of the probe of those figures and the inclusion of an ECG electrode in the probe.

It is to be understood that the foregoing drawings, and the description below, are provided primarily for purposes of facilitating understanding the conceptual aspects of the invention and various possible embodiments thereof, including what is presently considered to be a preferred embodiment. In the interest of clarity and brevity, no attempt is made to provide more details than necessary to enable one skilled in the art, using routine skill and design, to understand and practice the described invention. It is to be further understood that the embodiments described are for purposes of example only, and that the invention is capable of being embodied in other forms and applications than described herein.

DESCRIPTION OF PREFERRED EMBODIMENTS

As indicated earlier, the body probes constructed in accordance with the present invention are capable of being applied to almost any selected area of a subject's skin for measuring changes in the pulsatile arterial blood volume thereat, without restricting the probe to a terminal extremity, such as the finger or toe of the subject's body. The probe includes a base for application to the selected area of the subject's skin at the measurement site, a pressure applicator carried by the base for applying a static pressure to the subject's skin at the measurement site, and a sensor carried by the pressure applicator for sensing changes in the pulsatile arterial blood volume at the measurement site. According to the present invention, the pressure applicator applies to the measurement site a static pressure of a magnitude to partially unload the wall tension of, but not to occlude, the arteries at the measurement site. The pressure applicator is configured to substantially prevent venous distention and blood pooling at the measurement site by applying sufficient external counter pressure to effectively collapse the underlying veins and limit the local venous blood flow to the arterial throughput while permitting free venous drainage with respect to the measurement site through tissues surrounding the measurement site. The latter is effected, in the described preferred embodiments, by applying the static pressure to a relatively restricted area of the subject's skin, which area occupies a relatively small fraction of the surface perimeter of the respective body part at the measurement site, to thereby permit free venous drainage from the measurement site via a wide region of unrestricted passageways surrounding the measurement site.

The drawings illustrate a number of probes constructed in accordance with the foregoing features of the invention.

The probe illustrated in FIGS. 1a-1c, and therein generally designated 10, includes a base 11 of a non-stretchable material; a pressure applicator 12 centrally of the base; and a sensor 13 centrally of the pressure applicator for sensing changes in the pulsatile arterial blood volume at the respective measurement site. The surface of base 11 facing the pressure applicator 12 and sensor 13, brought into contact with the subject's skin, includes an adhesive layer 14 for adhering the base to the subject's skin at the measurement site.

As described earlier, pressure applicator 12 applies a static pressure of an appropriate level to enhance arterial pulsatile pressure measurements, by unloading vascular wall tension, while at the same time preventing venous distention and pooling. Thus, since the pressure applicator is applied to a relatively restricted area of the subject's skin which area occupies a relatively small fraction of the surface perimeter of the respective body part at the measurement site, the static pressure applied at the measurement site permits free venous drainage from the measurement site via a wide region of unrestricted passageways surrounding the measurement site.

In probe 10 illustrated in FIGS. 1a-1c, the pressure applicator 12 includes a fluid chamber 15 connected via a tube 16 to a source of pressurized fluid (e.g., air), and a rigid cap 17 on the side of the applicator opposite to that carrying the sensor 13. Thus, when the base 11 has been firmly adhered to the subject's skin at the measurement site by the adhesive surface 14, pressure applicator 12 may be pressurized, via tube 16, to apply to the measurement site the appropriate pressure, as set forth above, to enable sensor 13 to sense changes in the pulsatile arterial blood volume without the effects of venous distention and pooling. The actual volume changes occurring within the above described pressurized pneumatic system may be measured and thus serve as an independent signal for measuring the changes in the pulsatile arterial blood volume without the effects of venous distention and pooling as described in a previous application (Foreign Application [IL] 118976 Jul. 30, 1996, see FIG. 5 thereof). The latter sensing modality may be used independently or in combination with other sensing modalities Sensor 13 could be any type of sensor, such as any of those described or mentioned in the above-cited patents and applications (the contents of which are incorporated herein by reference), for detecting mechanical perturbations, volumetric changes, pressure changes, optical density changes or surface-reflectivity changes, laser Doppler device, or other flow meter devices, electromagnetic changes, Hall effect changes, strain gauge devices piezo-electric elements etc.

The various medical conditions or physiological states detectable by probe 10, as well as the other probes constructed in accordance with the present invention as described below, include myocardial ischemia, sleep apnea, hypopnea, upper airway resistance syndrome, endothelial dysfunction (ED), and sleep disorders, as well as certain physiological states, such as mental stress, sympathetic nervous system reactivity, responses to physical, pharmacological agent, or mental stressors, blood pressure, REM stage sleep, etc. or any of the medical conditions or physiological states described or mentioned in the above-cited patents and applications (the contents of which are incorporated herein by reference). As will be described below with respect to FIGS. 11a-14, particularly important advantages are obtainable when the invention is implemented in pulse oximetry probes.

FIGS. 2a-2c illustrate another probe constructed in accordance with the present invention, and therein generally designated 20, also including a base 21 for application to a selected area of the subject's skin at the measurement site; a pressure applicator 22 carried by the base for applying a static pressure to the subject's skin at the measurement site; a sensor 23 carried centrally of the pressure applicator for sensing changes in the pulsatile arterial blood volume at the measurement site; and an adhesive layer 24 for adhering the base 21 to the subject's skin at the measurement site. In this case, however, the pressure applicator 22 comprises a fluid chamber with at least one elastic wall constructed to utilize Laplace's law. Thus, as described, e.g., in the above-cited U.S. Pat. No. 6,461,305, an appropriate implementation of Laplace's law is capable of producing a fixed predetermined pressure on an external elastic membrane irrespective of the underlying tissue characteristics. Long term preservation of fluid volume prior to use in such device could be achieved by way of rupturing an internal air-sac (packaging bubbles), or by deforming a volume-occupying plastic former, or by using bistable volume-occupying elements, as described for example in our pending published application No. U.S. 2002/0072681 A1.

FIGS. 3a-3c illustrate another probe, therein generally designated 30, constructed in accordance with the present invention to also include a base 31 for application to the selected area of the subject's skin; a pressure applicator 32 for applying a static pressure to the subject's skin at the measurement site; a sensor 33 for sensing changes in the pulsatile arterial blood volume at the measurement site; and an adhesive layer 34 for adhering the base to the subject's skin at the measurement site. In this case, however, the pressure applicator 32 includes a coil spring 35 within a rigid housing 36 carrying the sensor 32 at one end of the spring projecting from the housing for applying, to the measurement site sensed by sensor 33, the appropriate pressure for unloading vascular wall tension, and thereby enhancing arterial pulsatile pressure measurements, while at the same preventing venous distension and pooling, as described above.

Spring 35 of the pressure applicator 32 is preferably of a relatively large length in its uncompressed condition such that the effective pressure generated by it, when compressed, is substantially unaffected by relatively small variations in compressed length due to the mechanical characteristics of the underlying tissues. This is particularly so when a substantial fraction of spring 35 in its compressed state is contained within housing 36.

FIGS. 4a-4c illustrate a probe, therein generally designated 40, of similar construction as in FIGS. 3a-3c, but including a cylindrical column of elastic material, such as a sponge material, instead of the spring-loaded mechanism of FIGS. 3a-3c. Thus, the probe of FIGS. 4a-4c also includes a base 41, a pressure applicator 42, a sensor 43, and an adhesive coating 44, corresponding to elements 31-34, respectively in FIGS. 3a-3c, except that, in the case of FIGS. 4a-4c, the pressure applicator 42 includes a cylindrical column 45 of a resilient elastomeric material, such as an elastomeric spongy material, instead of the spring 35 in FIGS. 3a-3c. within a rigid housing 46 corresponding to the rigid housing 36 of FIG. 3a-3c. The resilient elastomeric material 45 in probe 40 should also be of a relatively large uncompressed length such that the effective pressure generated by it, when compressed, is substantially unaffected by relatively small variations in the compressed length due to the mechanical characteristics of the underlying tissues. As in the previous case, this is particularly so when a substantial fraction of the cylindrical elastomeric column 45 in its compressed state is contained within rigid housing 46.

Figure 5B:
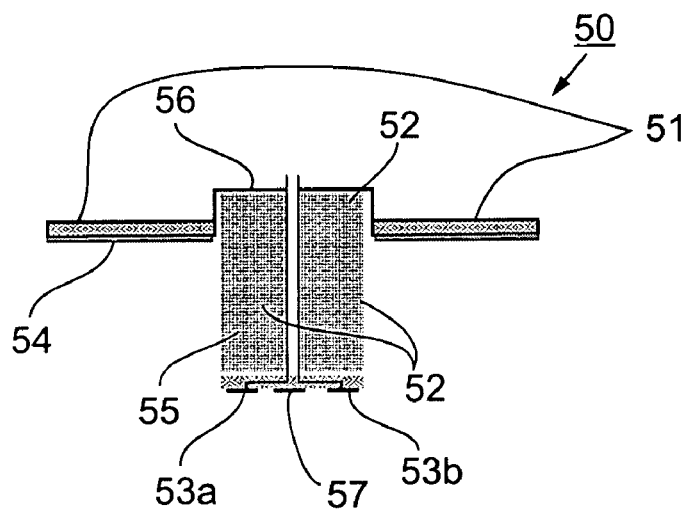
Figure 5C:
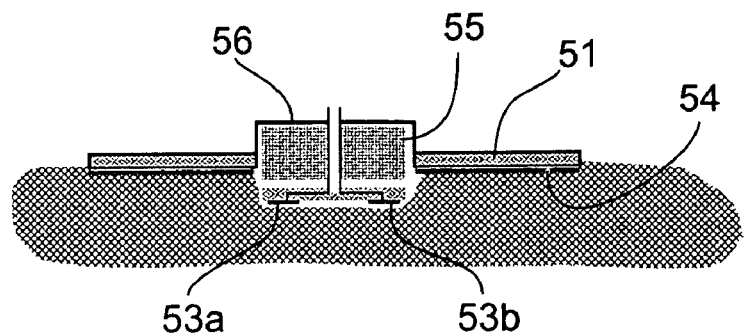

FIGS. 5a-5c illustrate a probe, generally designated 50, of similar construction as shown in FIGS. 4a-4c, also including a base 51 coated on its underside with an adhesive layer 54, a pressure applicator 52 in the form of a column 55 of an elastomeric or spongy material covered at its upper face by a rigid cap 56, and a sensor projecting from the lower face of the elastomeric column 55 for contact with the subject's skin at the measurement site. In probe 50, the sensor is an optical sensor, including an optical transmitter 53a and an optical receiver 53b for optically sensing changes in the pulsatile arterial blood volume at the measurement site.

Probe 50 illustrated in FIGS. 5a-5b further includes an ECG electrode 57 for sensing electrocardiograph (ECG) signals, concurrently with the measurement of changes in the pulsatile arterial blood volume by sensors 53a, 53b. The sensed ECG signal may also be used with the arterial blood volume measurements to detect or indicate a medical condition or physiological state of the subject, e.g., by producing a measurement of the pulse propagation velocity.

Figure 6:
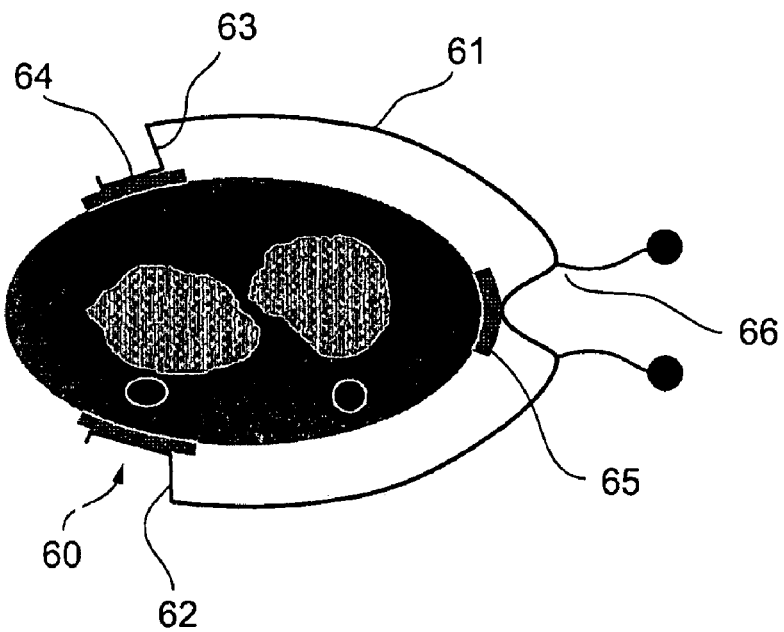
FIG. 6 diagrammatically illustrates one manner of clamping the probe to a restricted area on the surface of a subject's skin.

FIG. 6 illustrates a clamping arrangement which may be used, instead of or together with the adhesive coating applied to the underside of the probe base, for clamping the probe to a restricted area of the subject's skin (e.g., the subject's wrist), which restricted area occupies a relatively small fraction of the surface perimeter of the respective body part (wrist) at the measurement site. Such an arrangement permits free venous drainage from the measurement site via a wide region of unrestricted passageways surrounding the measurement site.

In FIG. 6, the probe is generally designated 60. It may be of any of the above-described constructions, with or without (preferably with) the adhesive coating (e.g., 14) on the underside of the base (e.g., 11). The clamp used, generally designated 61 in FIG. 6, may be, for example, a spring-loaded caliper. It includes one leg 62 engageable with the base of probe 60 for pressing it against the subject's skin at that location of the body part (e.g., wrist); a second leg 63 engageable with a pressure pad 64 at the opposite side of the subject's body part to apply a counter-force to the respective body part; and a third leg 64 engageable with another pressure pad 65 at a third point of contact with the body part, to thereby produce a three-point clamping arrangement on the respective body part.

The pressure applied by leg 62 against the base of the probe 60, together with the pressure generated by the pressure applicator portion of the probe (e.g., pressure applicator 12, FIGS. 1a-1c), should preferably be above normal venous pressure, but below the diastolic arterial blood pressure, to thereby enhance the arterial pulsatile pressure measurements by the sensor (e.g. 12, FIGS. 1a-1c) at the measurement site. Thus, since the pressure applied to the body part (e.g., wrist) does not extend for the entire perimeter of the body part, such a clamping arrangement permits free venous drainage with respect to the measurement site (i.e., occupied by the sensor) through the tissues surrounding the measurement site, thereby preventing venous distention and blood pooling at the measurement site.

Figure 7:
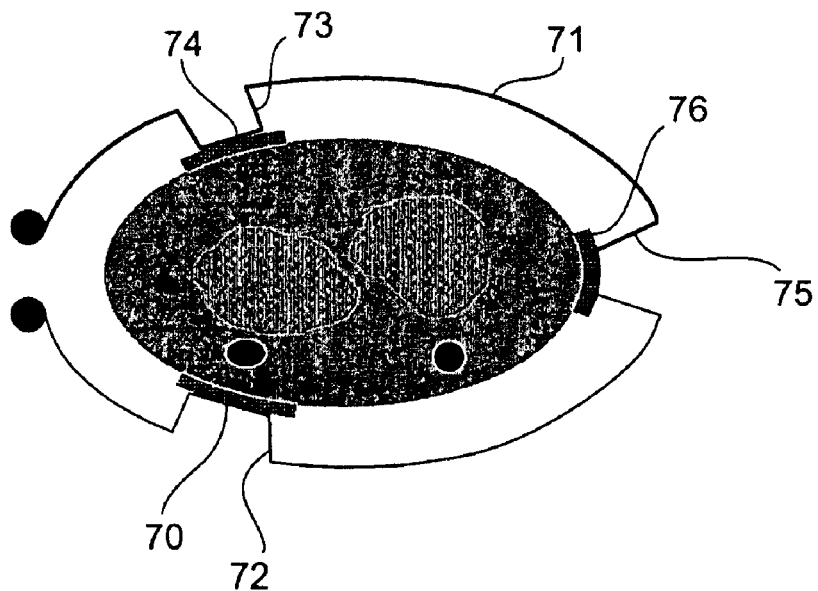
FIG. 7 diagrammatically illustrates another manner of clamping the probe to a restricted area of the subject's skin.

FIG. 7 illustrates a slightly different clamping arrangement for clamping the probe, therein generally designated 30, to the body part (e.g., wrist). The clamping arrangement illustrated in FIG. 7 is a spring loaded bracelet, generally designated 71, encircling the respective body part (e.g., wrist). Bracelet 71 also includes one leg 72 for applying the appropriate pressure to the sensor 70 at one side of the body part, another leg 73 for applying a counter-pressure to a pressure pad 74 at the opposite side of the body part, and a further leg 75 for applying pressure to a further pressure pad 75 at a third point of the body part, to thereby provide a three-point mounting of the bracelet. In all other respects, the spring loaded bracelet 71 illustrated in FIG. 7 operates in the same manner as described above with respect to FIG. 6 to enhance the arterial pulsatile pressure measurements by probe 70, by unloading vascular wall tension while at the same time preventing venous distension and pooling.

As indicated earlier, an important advantage of the novel probe constructed in accordance with the present invention is that a plurality of such probes may be used at different locations of the subject's body for measuring changes in the pulsatile arterial blood volume at each such location. Such measurements at the different measurement sites can provide further information useful for detecting and indicating various medical conditions of the subject.

For example, a plurality of body surface probes can be used to obtain simultaneous and comparative measurements from arterial-venous shunt rich palmar surfaces of the hand or plantar surfaces of the foot, and other parts of those limbs which have corresponding surfaces which are arterio-venous shunt poor. Such comparisons may help to accentuate the intensity of autonomic nervous system activation, since arterio-venous rich sites have greater autonomic control. Further applications of the invention utilizing two or more such probes are described below particularly with reference to FIGS. 10-16.

Figure 8:
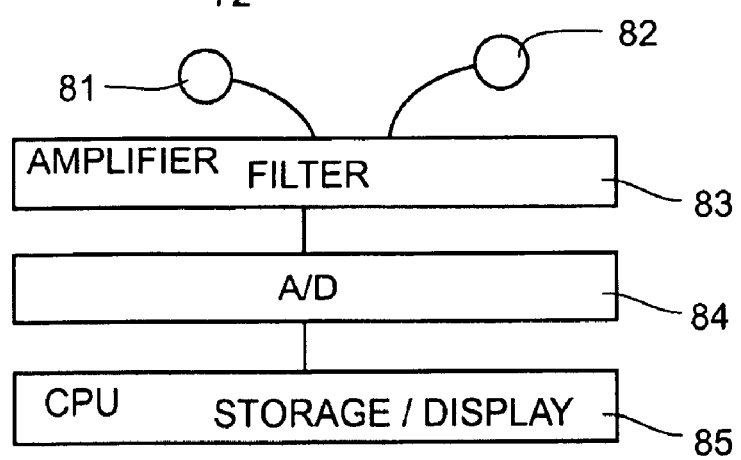
FIG. 8 is a block diagram illustrating one form of apparatus constructed in accordance with the present invention to utilize the measurements of a plurality of probes for detecting or indicating the medical condition or physiological state of the subject.

FIG. 8 is a block diagram illustrating the main components of apparatus utilizing one, two, or more such probes. In the example illustrated in FIG. 8, the apparatus includes two such probes 81, 82, which may be of any of the foregoing constructions. Each probe, therefore, would include a base for application to the selected area of the subject's skin at the measurement site, a pressure applicator carried by the base for applying the required static pressure to the subject's skin at the measurement site, and a sensor for sensing changes in the pulsatile arterial blood volume at the measurement site, as more particularly described above. If one (or both) of the sensors included an ECG electrode (corresponding to ECG electrode 57 in FIGS. 5a-5c), the apparatus could be utilized not only for measuring changes in the pulsatile arterial blood volume at the respective measurement site, but also for generating ECG signals, e.g., to determine the pulse transition time and/or pulse propagation velocity. Such information would also be useful in detecting or indicating the medical condition or physiological state of the subject. As will be described, several other biopotential based or non-biopotential based signals may usefully be recorded in combination from a common probe as illustrated for the case of an ECG electrode in FIGS. 5a-5c.

As shown in FIG. 8, the outputs of the probes 81, 82 are applied to an amplifier and filter circuit 83, converted to digital by an A/D circuit 84, and inputted into a data processor system 85 having a CPU, storage display, etc.

Probes 81, 82 illustrated in FIG. 8 may be wire-connected to the data processor 85 via circuits 83 and 84, or may communicate with data processor via a wireless communication link, e.g., RF, infra-red, acoustical, etc. In the latter case, the energy supply for sensing changes in the pulsatile arterial blood volume at the respective measurement site, and for transmitting such measurements to the data processor system, would be contained within the probe itself, thereby freeing the subject from attachment to the data processor. In the case where either or both probes 81, 82 are wire-connected to the processor 85, the latter and its supporting system may be mounted on the subject, as previously described in U.S. Pat. No. 6,461,305 thus providing the subject with freedom of movement.

A sleep/wake detector such as an actigraph device can also be incorporated into a probe device or into the subject mounted processor 85 and its supporting system, as described for example in our pending published Application No. U.S. 2003/0004423 and in WO 01/64101 (Method and Apparatus for the Non-Invasive Detection of Particular Sleep-State Conditions by Monitoring the Peripheral Vascular System). In addition to the pulsatile arterial volume signal, other physiological parameters can also be sensed by the body surface probes. In principal any of the known physiological parameters which can be can be sensed from the body's surface can also be sensed, together with the arterial pulsatile volume signal. Examples of such parameters include: blood oxygen saturation levels sensed by the method generally known as pulse oximetry; sounds such as those related to breathing; biological potentials, such as electro-cardiography (ECG), electro-encephelography (EEG), electro-myography (EMG), electro-oculography (EOG), using at least a bipolar measurement setting; pulse transit time (PTT); local skin temperature; galvanic skin response signal (GSR); and any other known biological parameter that can be sensed from the surface of the skin. The simultaneous measurements derived from different measurement sites may provide further useful information by facilitating the measurement of bio-potentials such as ECG, EOG, EMG, EEG, etc. which require at least a single dipole for adequate measurement. As mentioned, non-biopotential signals such as skin temperature, galvanic skin response, and acoustic recordings, can further provide useful information. The above listed signals may be derived from the same probe device as that used for sensing changes in the pulsatile arterial blood volume at the measurement site in the manner illustrated for an ECG electrode in FIGS. 5a-5c.

The following experiment was conducted to demonstrate that the venous pooling artifact free measurement of arterial pulse signals and their changes can be derived from virtually any point on the body surface using the above-described probes, in a manner similar to that of the finger (or toe) probes described in the above-identified patents and applications.

Figure 9:
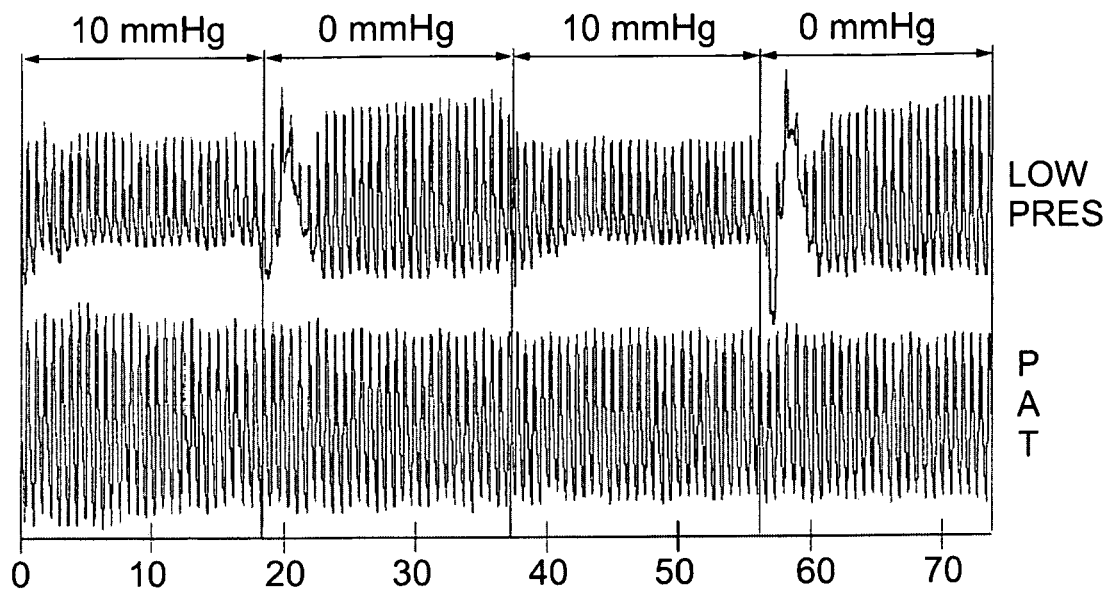
FIG. 9 includes two traces which demonstrate, as will be described more particularly below, that measurements of arterial blood volume changes substantially free of venous pooling can be made at virtually any location of a subject's body.

FIG. 9 shows the acute affect of induced venous pooling and its resolution, using a previously described finger probe. More particularly, this figure shows the time-course of pulse wave amplitude in two adjacent fingers-when a proximal cuff on the upper arm is alternately inflated to a pressure of 40 mmHg and then deflated back to 0 mmHg. The result of inflating the proximal cuff to 40 mmHg is to induce venous distention in the tissues distal to the cuff. The upper trace shows the pulse-wave amplitude recorded from the finger probe when a minimal external pressure is applied while the lower trace shows the pulse-wave amplitude recorded by the finger probe when pressure field of near diastolic pressure is applied over the entire surface of the two distal most phalanges. It is clear that in the finger with the minimal external pressure field, the periods of induced venous distention are associated with substantial attenuation of the pulse-wave amplitude, compared to when there is no applied venous distention. In sharp contrast to this, the simultaneous recording from the finger within the pressure field is essentially unaffected by the induced venous distention.

Figure 10:
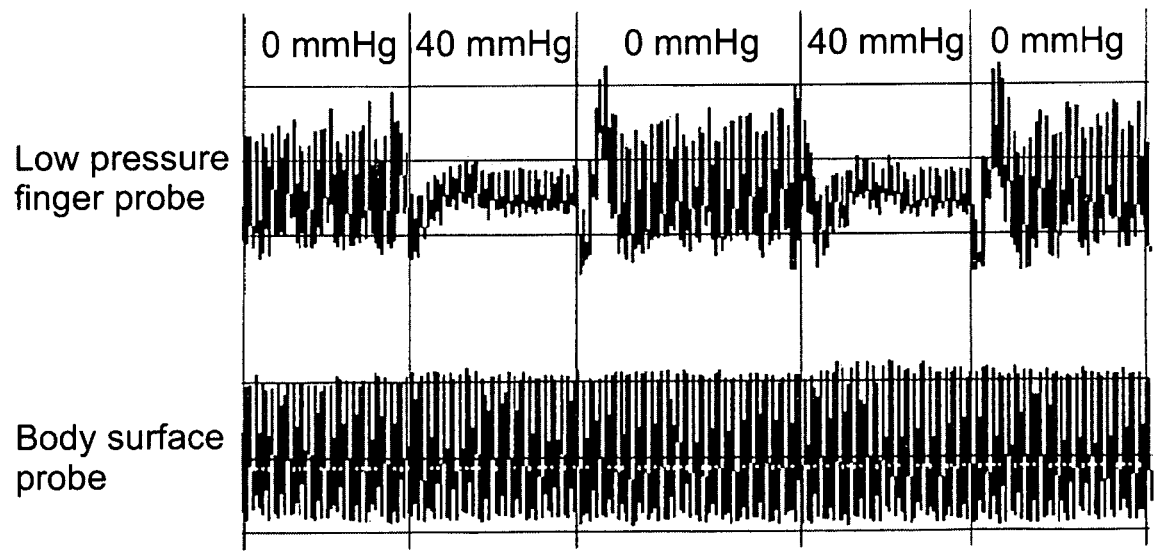
FIG. 10 illustrates, in the upper trace the output signal from a probe applied to the finger pressurized to a minimum pressure field, and in the lower trace the output signal from a probe mounted on the palm and pressurized to a near diastolic pressure field.
Figure 11A:
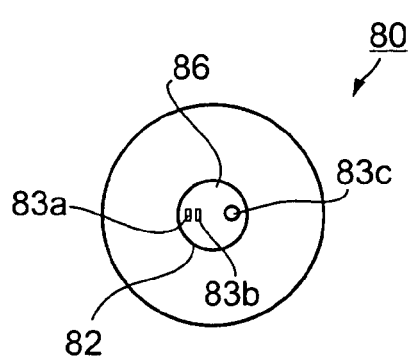
Figure 11B:
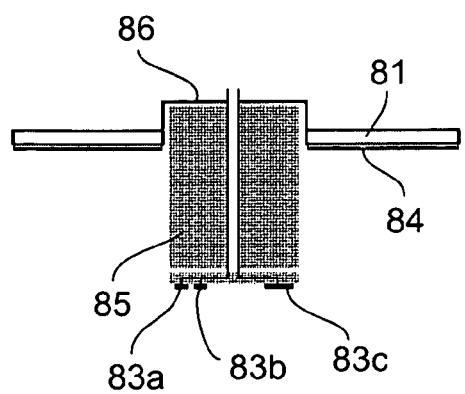
Figure 11C:
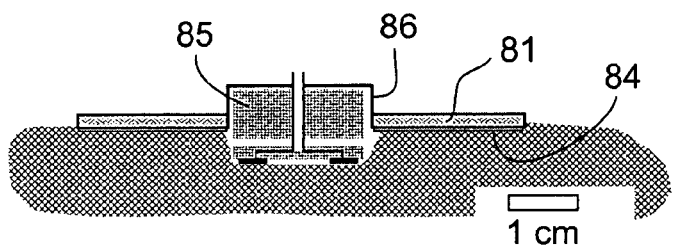
Figure 11D:
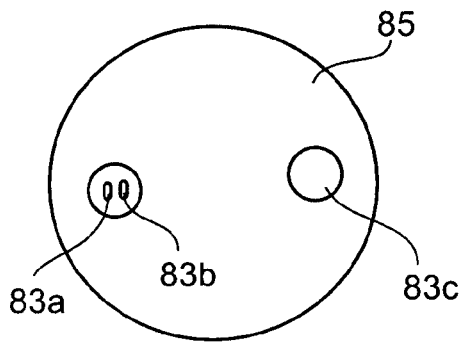
FIGS. 11d and 11e are plan and side views, respectively, more particularly illustrating the construction of the optical sensor.
Figure 11E:
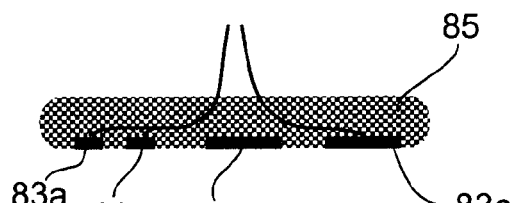

FIG. 10 shows a similar the results of a similar experiment when the time-courses of the pulse wave amplitude sensed by a body surface probe constructed in accordance with the invention (e.g., FIGS. 4a-4c) and mounted, respectively on the palm (lower trace) and a finger (upper trace) recorded from a finger probe in which a minimal external pressure is applied, when a proximal cuff on the upper arm is alternately inflated to a pressure of 40 mmHg and then deflated to 0 mmHg. Inflating the cuff to 40 mmHg induces venous distention in the tissues distal to the cuff. The upper trace is the pulse signal from a prior finger probe within minimal external counter pressure environment; and the lower trace is the pulse signal from the novel palm-mounted body surface probe within a near diastolic pressure field applied to the local measurement site only.

In both cases illustrated in FIGS. 9 and 10, in the absence of the pressure field, periods of induced venous distention are associated with substantial attenuation of the pulse signal. In sharp contrast, the simultaneous recording from the finger or the palm region within the respective pressure fields generated by the different probe devices were both essentially unaffected by the induced venous distention.

The acute effect of this locally induced signal attenuation is further complicated by a tendency for induced veno-arteriolar vasoconstriction to propagate centripitally over time.

FIGS. 11a-11e illustrate a probe, therein generally designated 80, similar to probe 50 of FIGS. 5a-5b, but particularly suitable for making pulse-oximetry measurements.

Pulse oximetry is based on the characteristic that oxygenated hemoglobin absorbs more infrared light and allows more red light to be transmitted; while deoxygenated (or reduced) hemoglobin behaves in an opposite manner and absorbs more red light and allows more infrared light to be transmitted. At a wavelength of about 805 nm light absorption or transmission is unaffected by the level of oxygen saturation (i.e. the isobestic wavelength).

By alternatively exposing the measurement site to red and infrared (or to the isobestic wavelength) light from appropriate LEDs switched in rapid succession, the level of transmitted (or scattered) light can be measured using a light sensitive element. By calculating the comparative differences in absorptions at respectively high and low points of the pulse wave at both respective wavelengths, and using an empirically derived conversion equation, it is possible to then compute the proportion of hemoglobin which is oxygenated.

There are two main methods of performing pulse oximetry: (a) transmission mode, in which the light source and optical detector are placed on opposite sides of the tissue; and (b) reflection mode in which they are placed along side of each other.

The wavelengths used are within the ranges of 600-750 nm (red) and 850-1000 nm (infrared). Typical values are 660 nm for red, and 920 or 940 nm for infrared, or a combination of 650 nm and 805 nm.

Thus, probe 80 illustrated in FIGS. 11a-11e also includes a base 81 coated on its underside with an adhesive layer 84, a pressure applicator 82 in the form of a column 85 of an elastomeric or spongy material covered at its upper face by a rigid cap 86, and a sensor projecting from the lower face of the elastomeric column 85 for contact with the subject's skin at the measurement site. As shown particularly in FIGS. 11d and 11e, the sensor includes two transmitters 83a, 83b (e.g., LEDs) of different wavelengths, and a receiver 83*c* (e.g., a photo detector) spaced from the two LEDs by an opaque surface 83*d* to be pressed against the subject's skin. It will thus be seen that, by rapidly switching the two LEDs in succession, the level of light transmitted (or scattered) by the tissue occupying surface 83*d* will be detected by photo detector 83*c*, to enable a computation to be made as to the blood oxygen saturation level of the tissue placed against the opaque surface 83*d*.

Figure 12:
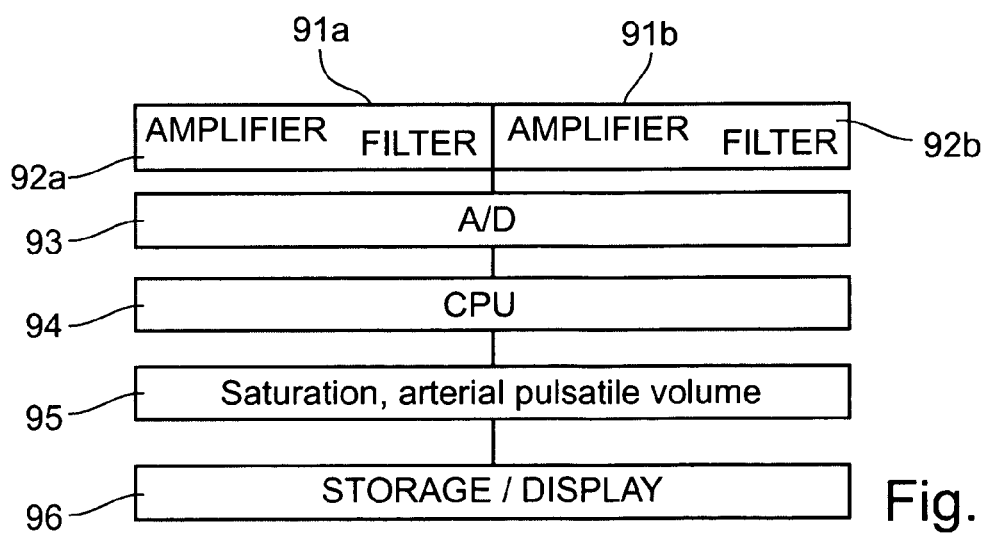
FIG. 12 is a block diagram illustrating apparatus constructed in accordance with the present invention to utilize the measurements of the probe of FIGS. 11a-11e.

FIG. 12 is a block diagram illustrating the apparatus, generally designated 90, for utilizing the outputs of photo detector 83*c* for producing measurements of blood saturation level and arterial pulsatile volume. As shown in FIG. 12, the photo detector 83*c* produces, two outputs each corresponding to the level of the light received from one of the two LEDs 83*a*, 83*b*. These photo detector outputs are applied as inputs 91*a*, 91*b*, to a separate amplifier/filter channel 92*a*, 92*b* for amplification and filtration, before being converted via A/D converter 93 to digital form and inputted into a CPU 94. CPU 94 employs the appropriate conversion equations (e.g., empirically derived) to compute the blood saturation level, arterial pulsatile volume, etc., as shown by block 94. These values are then stored and/or displayed, as shown by block 96.

FIGS. 13*a* and 13*b* illustrate a probe construction similar to that of FIGS. 11*a*-11*e*, except one that it also includes a conductive element such as an ECG electrode. Thus, as shown in FIGS. 13*a* and 13*b*, the probe, then generally designated 100, also includes the two light transmitters 103*a*, 103*b*, and the receiver 103*c*. Here, however, the space between the latter elements is occupied by the conductive element such as an ECG electrode 104*a* to enable the probe also to measure electrical potentials such as the ECG signals from the subject.

The construction of probe 100 of FIGS. 13*a*, 13*b* is otherwise the same as probe 80 of FIGS. 11*a*-11*e*.

FIG. 14 illustrates apparatus for processing the output of probe 100, which apparatus is similar to that of FIG. 12 for processing the output of probe 90, except that the apparatus of FIG. 14 also includes inputs from the two ECG electrodes 104*a*, 104*b*. Accordingly, the other elements illustrated in FIG. 14 are identified with the same reference numerals as in FIG. 12, with the addition of the input from the ECG electrode 104*a* together with that from another probe being identified as inputs 91*c*, 91*d*, respectively.

Possible Applications of the Novel Body Surface Probes

Figure 15:
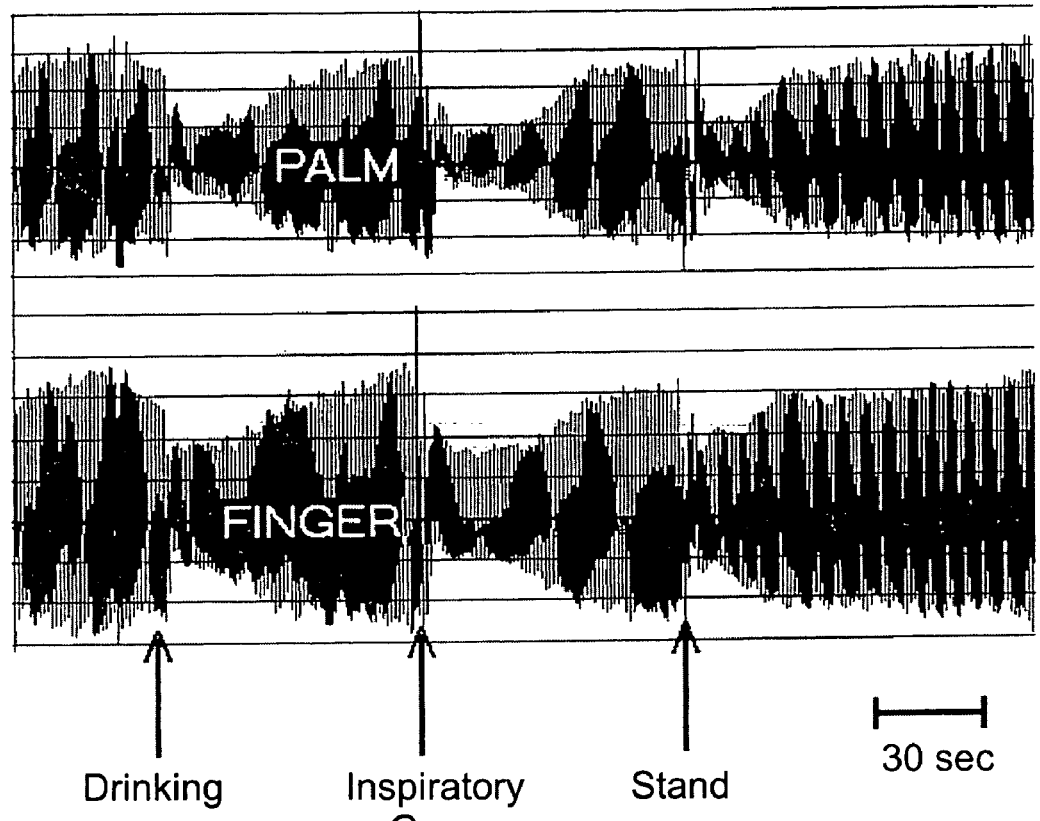
FIG. 15 illustrates the manner of using two probes constructed in accordance with the present invention, one applied to the palm and the other applied to the finger, to detect changes in the pulsatile arterial blood volume at two different locations on the subject's body having different short term responses to reflex events.
Figure 16:
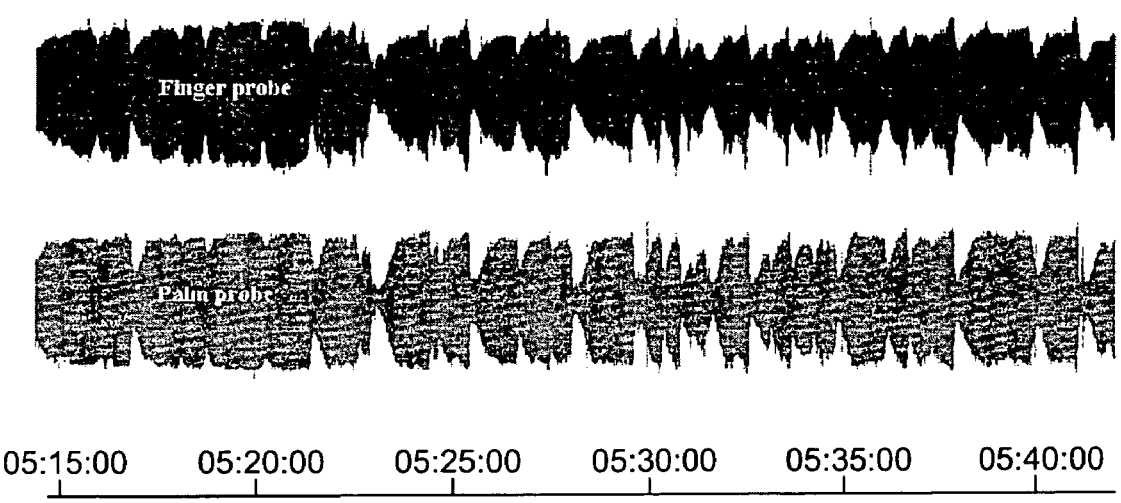
FIG. 16 illustrates the outputs of two probes constructed in accordance with the present invention applied to different parts of the subject's body (finger and palm) during a 30-minute period of sleep.

Following is a partial list of possible applications for the above described probe, apparatus and method:

1. The novel body surface probes may constitute an alternative sensing probe for all applications of the peripheral arterial pulsatile volume or peripheral arterial tone measurements referred to in all our previous above-identified patents and applications, (e.g., sleep-medicine related, exercise-stress testing related, endothelial function testing related, responses to physical, pharmacological or mental agents or stressors, etc.). An example of short term responses to reflex events in simultaneous finger and palm measurements is shown in FIG. 15. The suitability of the body surface probe as an alternative to the previously described probes is further emphasized in FIG. 16. This shows the time course of finger and palm arterial pulse amplitude as a function of time during a 30 minute period of sleep during which frequent apneas occurred. The frequent periodical falls in signal amplitude, occurring at the same times in both signals are the result of those apnea events during sleep.

2. The novel body surface probes may also be applicable to arterio-venous shunt rich palmar surfaces of the hand or plantar surfaces of the foot and may be less disturbing than the previously-described finger probes, easier to apply, less prone to accidental or intentional removal (particularly among young subjects such as babies or infants), and more suitable if fingers are abnormally small or large, or if misshapen or deformed, or for young children with small fingers or those tending to remove finger probes.

3. The novel body surface probes can also be used to obtain simultaneous and comparative measurements from for example, arterio-venous shunt rich palmar surfaces of the hand or plantar surfaces of the foot and corresponding arteriovenous shunt poor dorsal aspects of those limbs. Such comparisons may help to accentuate the intensity of autonomic nervous system activation, since arteriovenous rich sites have greater autonomic control.

Figure 17:
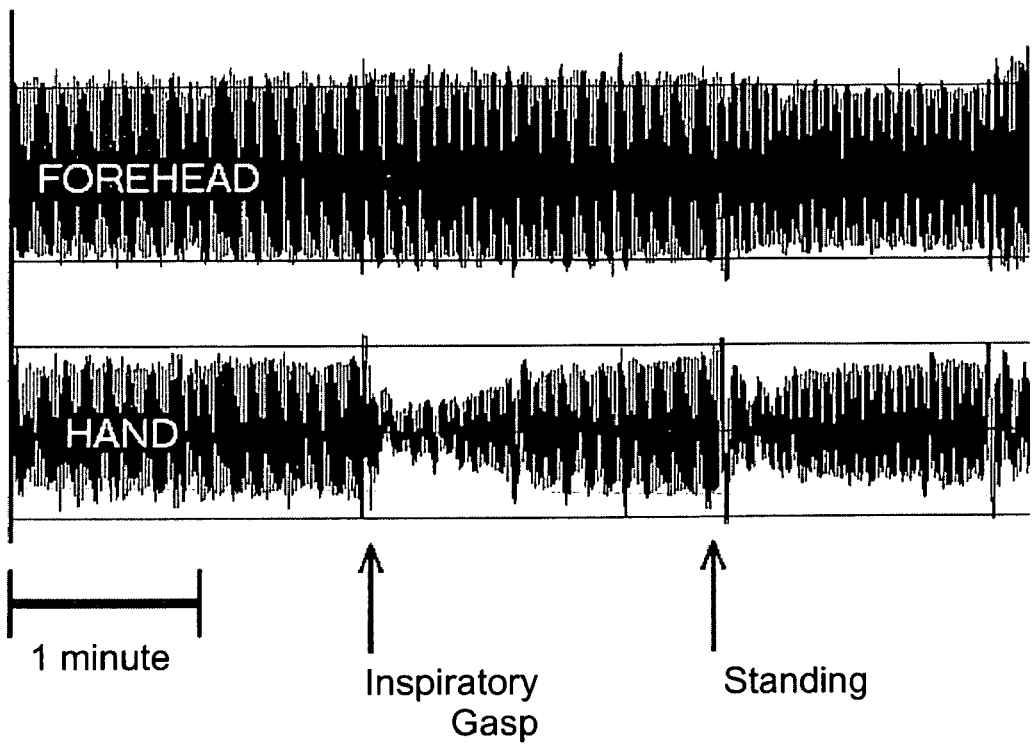
FIGS. 17 and 18 illustrate the outputs of two probes constructed in accordance with the present invention applied to different parts of the subject's body (forehead and hand) in which the vascular beds have different reactivity to autonomic stimulation.
Figure 18:
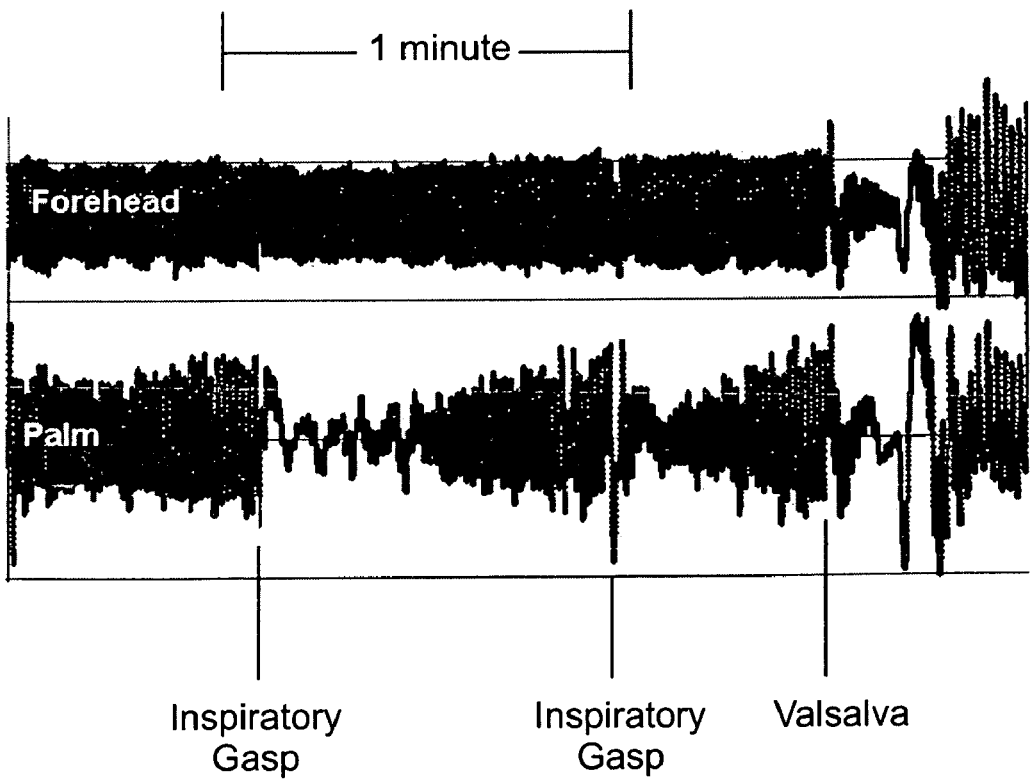

4. Likewise, two or more such novel body surface probes may be simultaneously applied to other combinations of body sites, such as the forehead, where vascular beds are very much less reactive to autonomic stimulation, and the palmar surface of the hand where autonomic regulation is extremely high. Such comparisons can be used to differentiate between reflex mediated vasoconstriction which affects the hand's palmar surface only, as shown in relation to the inspiratory gasp events indicated in FIGS. 17 and 18, and a diminution of the arterial pulse wave amplitude due to a reduction in stroke volume or a fall in pulse pressure which would affect both sites. This is illustrated in FIG. 18 in relation to the Valsalva maneuver.

Figure 19:
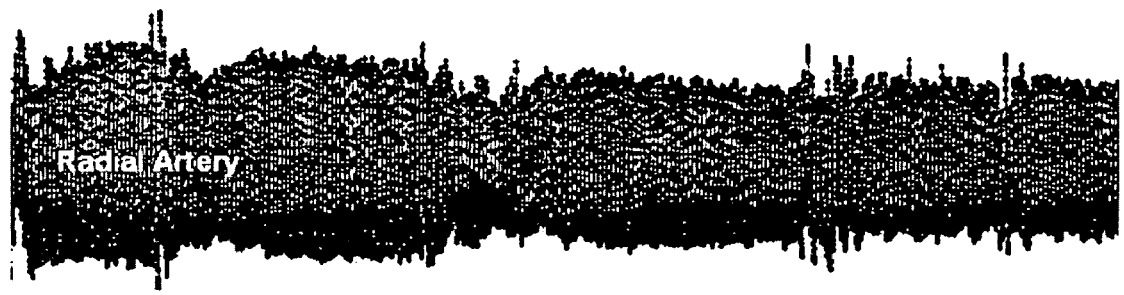
FIG. 19 illustrates the output of a probe constructed in accordance with the present invention applied to a radial artery or other major superficial artery overlying a bony region.

5. Body surface probes may be applied to a radial artery or other major superficial artery preferably overlying a bony region, and to a peripheral arterial vascular bed such as the palmar surface of the hand, to get an index of conducting or conduit artery behavior which is relatively less affected by autonomic nervous system in comparison to the peripheral arterial site which is more strongly affected by the autonomic nervous system. A recording derived from a radial artery is shown in FIG. 19.

6. Similar to application 4 above, a pair of the novel body surface probes may be applied respectively to a radial artery or other major superficial artery preferably overlying a bony region, and to a peripheral arterial vascular bed such as the palmar surface of the hand. A comparison of the probe outputs would provide an index of conduit artery behavior which is relatively less affected by autonomic nervous system, in comparison to the peripheral arterial site which is more strongly affected by the autonomic nervous system. Such probes may be used simultaneously at a large arterial site and in multiple peripheral sites as described in applications 2, 3 and 4 above.

7. The application of a body surface probe may be useful for evaluating the level of endothelial function to facilitate Endothelial Dysfunction diagnostic assessment as described in considerable detail in WO 02/34105 (Method and Apparatus for Non-Invasively Evaluating Endothelial Activity in a Subject).

In this application, the novel body surface probe sensor may be used in place of the various sensor types described in that patent dealing with endothelial function evaluation. The novel body surface probe devices may be used to perform all of the assessments described there. Its use may also be more convenient in many cases.

The application of the novel body surface probe over a radial artery, or any other major superficial artery preferably overlying a bony region, may be especially useful for evaluating endothelial function or determining if a state of endothelial dysfunction (ED) is present or not, in regard to large conduit arteries, or in regard to microvascular arterial blood vessels.

The combined assessment of endothelial function or the determination of whether a state of endothelial dysfunction (ED) is present or not, in relation to both large conduit vessels and to microvascular arterial blood vessels, can be made simultaneously by using a plurality of the body surface probes at the appropriate sites. The combined assessment of endothelial function or the determination of whether a state of endothelial dysfunction (ED) is present or not, in relation to both large conduit vessels and to microvascular arterial blood vessels, can be of further value since this not only facilitates determining the separate responses of both types of vascular beds, it also facilitates the determination of their comparative responses.

8. The novel body surface probes may be also applied to a large superficial artery such as the radial artery as a robust means of determining BP trends. The amplitude of a pulsatile blood volume signal from a given large artery is primarily a function of arterial blood pressure. In contrast, the level of peripheral arterial tone in peripheral vascular beds comprising arterial vessels of a wide spectrum of calibers is primarily a function of the resistance of a given vascular bed and the blood pressure. By sensing changes in the pulstile arterial blood volume at a large vessel and at a peripheral site down stream from that large vessel, it is possible to determine the separate and comparative contributions of generalized system blood pressure changes and peripheral vascular resistance changes.

Figure 20:
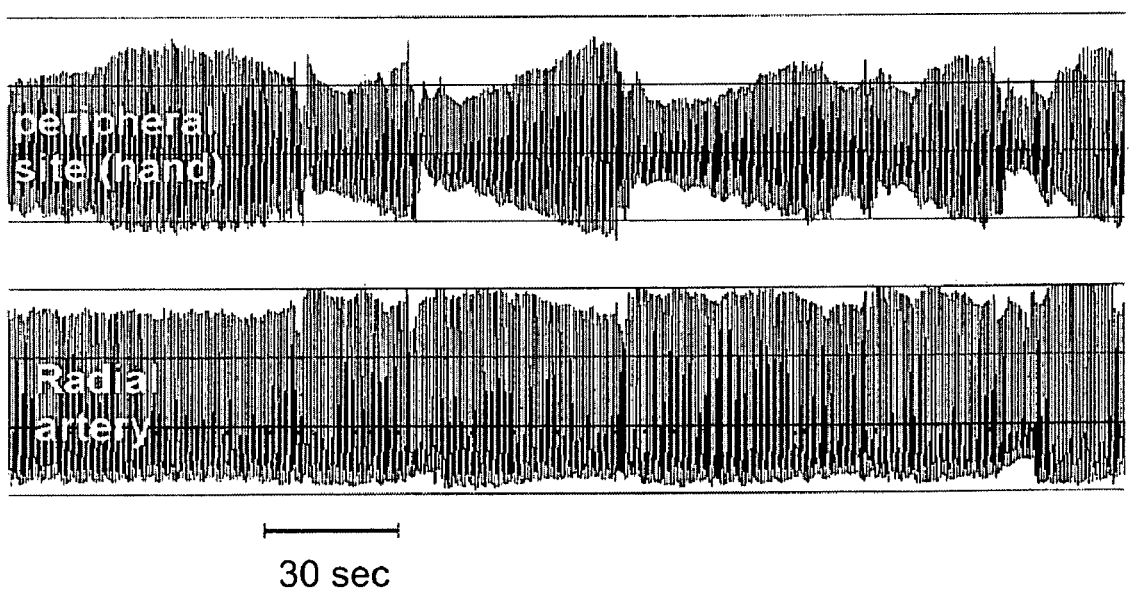
FIG. 20 illustrates the outputs of two probes constructed in accordance with the present invention applied to a hand and radial artery, respectively.

FIG. 20 illustrates an example of the latter application. This figure shows the peripheral signal recorded from the palmar surface of the hand (upper trace) and a simultaneous recording from the radial artery (lower trace). It is notable that the recording from the large artery is far less variable than that recorded from the peripheral location. It is also of interest that the trends of the respective large and small artery signs are often reciprocal in direction. This is consistent with the reciprocal relationship existing between peripheral resistance and blood pressure when cardiac output is stable. Thus combined measurements at these sights can provide a more complete understanding of the physiological state of the subject.

9. The novel body surface probes may also be applied to mid temporal arteries to monitor cerebral blood flow.

10. The novel body surface probes may also be used to measure pulse propagation velocity when two probes are placed in series at a known distance from each other along a major arterial pathway. (Propagation velocity is a potential blood pressure measurement surrogate and compliance index).

11. The novel body surface probes may also be used to measure the time course of mechanical perturbations, volumetric changes, pressure changes, optical density changes etc. consequent to the pulsatile arterial volume changes, as well as their variations, for the various diagnostic applications previously described, as well as for the purpose of providing input information for biofeedback treatment.

Advantages of Body Surface Probes in Pulse Oximetry Measurements

The use of the novel body surface probes for measurements by pulse oximetry provides two particularly important advantages:

1) The applied pressure field physically removes local venous blood in the measurement site. This is an important factor in the accurate measurement of the oxygen content of arterial blood since variations in venous blood can occur and these can contribute to the pulsatile difference measurements As a result a more accurate measurement is possible.

The optical density of the tissues is a combination of solid tissues, pulsatile arterial blood volumes, and fixed essentially non-arterial blood volumes. The solid tissues are by definition constant, and their contribution to light absorption is likewise constant. In contrast, the non-pulsatile arterial blood volume which is in very large part venous blood is capable of considerable variation. In vascular beds where there are direct arterio-venous pathways such as in the fingers, low pressure venous pulsation can also potentially occur. By ensuring that only pulsatile arterial blood is being measured this potential source of error is removed.

2). The novel body surface probes can provide an additional advantage for pulse oximetry measurement since they can be placed at body sites which directly overly superficial arteries, thus facilitating direct measurement from an arterial source.

In general pulse oximetry is performed on the fingers, toes or ear lobes. These measurement sites are mostly composed of microcirculatory vascular beds in which there is a mixture of blood vessel types including arterial, capillary, arteriovenous and venous vessels. The admixture of arterial and venous blood at such sites is the reason why oximetry is based on the pulsatile component of the signal.

Given the increased range of body sites made available by the body surface probes, it is possible to select a measurement site which directly overly superficial arteries. Provided that such arterial vessels are sufficiently thin walled, improved accuracy can be achieved since the blood is by definition arterial.

While the invention has been described with respect to several preferred embodiments and several preferred applications, it will be appreciated that these are set forth merely for purposes of example, and that many other variations, modifications and applications of the invention can be made.

What is claimed is:

1. A probe for application to a selected area of a subject's skin covering a body part, which selected area serves as a measurement site for measuring changes in the pulsatile arterial blood volume thereat, comprising:
   a base for application to the selected area of the subject's skin at said measurement site;
   a pressure applicator carried by said base for applying a static pressure to the subject's skin at said measurement site when said base is applied thereto;
   and a sensor carried by said pressure applicator for sensing changes in the pulsatile arterial blood volume at said measurement site when the base is applied thereto;
   said pressure applicator being designed to apply to said measurement site, when the base is applied thereto, a static pressure of a sufficient magnitude to partially unload the wall tension of, but not to occlude, the arteries at said measurement site; said pressure applicator being configured to substantially prevent venous distention and blood pooling at said measurement site by applying sufficient external counter pressure to effectively collapse the underlying veins and limit the local venous blood flow to the arterial throughput while permitting free venous drainage with respect to said measurement site through tissues surrounding said measurement site;
   said probe being configured to be applied to a relatively restricted area of the subject's skin, to apply said static pressure to said relatively restricted area , which area does not completely encircle the body part at said measurement site, said pressure applicator occupying a relatively small fraction of the surface perimeter of the respective body part at said measurement site, to thereby permit free venous drainage from said measurement site via a wide region of unrestricted passageways surrounding the measurement site;

wherein said pressure applicator comprises a fluid chamber with at least one elastic wall constructed to utilize Laplace's law and including a self-contained fluid for applying said static pressure to said measurement site such that the level of pressure applied by said probe is substantially unaffected by the mechanical characteristics of the underlying tissues.

2. The probe according to claim 1, wherein said pressure applicator applies to said measurement site a static pressure which is above the subject's local venous pressure and slightly below the subject's diastolic blood pressure.

3. A probe for application to a selected area of a subject's skin covering a body part, which selected area serves as a measurement site for measuring changes in the pulsatile arterial blood volume thereat, comprising:

a base for application to the selected area of the subject's skin at said measurement site;

a pressure applicator carried by said base for applying a static pressure to the subject's skin at said measurement site when said base is applied thereto;

and a sensor carried by said pressure applicator for sensing changes in the pulsatile arterial blood volume at said measurement site when the base is applied thereto;

said pressure applicator being designed to apply to said measurement site, when the base is applied thereto, a static pressure of a sufficient magnitude to partially unload the wall tension of, but not to occlude, the arteries at said measurement site; said pressure applicator being configured to substantially prevent venous distention and blood pooling at said measurement site by applying sufficient external counter pressure to effectively collapse the underlying veins and limit the local venous blood flow to the arterial throughput while permitting free venous drainage with respect to said measurement site through tissues surrounding said measurement site;

said probe being configured to be applied to a relatively restricted area of the subject's skin, to apply said static pressure to said relatively restricted area, which area does not completely encircle the body part at said measurement site, said pressure applicator occupying a relatively small fraction of the surface perimeter of the respective body part at said measurement site, to thereby permit free venous drainage from said measurement site via a wide region of unrestricted passageways surrounding the measurement site;

wherein said pressure applicator comprises a chamber including a spring therein for applying said static pressure to said measurement site; and wherein said spring for applying said static pressure to said measurement site is of a relatively large uncompressed length such that the effective pressure generated by it when it is compressed is substantially unaffected by relatively small variations in compressed length due to the mechanical characteristics of the underlying tissues.

4. A probe for application to a selected area of a subject's skin covering a body part, which selected area serves as a measurement site for measuring changes in the pulsatile arterial blood volume thereat, comprising:

a base for application to the selected area of the subject's skin at said measurement site;

a pressure applicator carried by said base for applying a static pressure to the subject's skin at said measurement site when said base is applied thereto;

and a sensor carried by said pressure applicator for sensing changes in the pulsatile arterial blood volume at said measurement site when the base is applied thereto;

said pressure applicator being designed to apply to said measurement site, when the base is applied thereto, a static pressure of a sufficient magnitude to partially unload the wall tension of, but not to occlude, the arteries at said measurement site; said pressure applicator being configured to substantially prevent venous distention and blood pooling at said measurement site by applying sufficient external counter pressure to effectively collapse the underlying veins and limit the local venous blood flow to the arterial throughput while permitting free venous drainage with respect to said measurement site through tissues surrounding said measurement site;

said probe being configured to be applied to a relatively restricted area of the subject's skin, to apply said static pressure to said relatively restricted area, which area does not completely encircle the body part at said measurement site, said pressure applicator occupying a relatively small fraction of the surface perimeter of the respective body part at said measurement site, to thereby permit free venous drainage from said measurement site via a wide region of unrestricted passageways surrounding the measurement site;

wherein said pressure applicator comprises a resilient elastomeric material for applying said static pressure to said measurement site; and wherein said resilient elastomeric material for applying said static pressure to said measurement site is of a relatively large uncompressed length such that the effective pressure generated by it, when it is compressed, is substantially unaffected by relatively small variations in compressed length due to the mechanical characteristics of the underlying tissues.

5. The probe according to claim 4, wherein said base is of a relatively non-stretchable material and carries said pressure applicator and sensor at the center thereof.

6. The probe according to claim 4, wherein said probe includes an optical sensor for sensing the blood oxygen saturation level.

7. The probe according to claim 6, wherein said probe also includes an electrode for sensing an electrical potential such as the electrocardiograph (ECG) signal of the subject.

8. The probe according to claim 4, wherein said probe also includes an electrode for sensing an electrical potential such as the electrocardiograph (ECG) signal of the subject.

9. The probe according to claim 4, wherein said probe also includes an acoustic sensor for sensing a sound signal of the subject.

10. The probe according to claim 6, wherein said probe also includes an acoustic sensor for sensing a sound signal of the subject.

11. A probe for application to a selected area of a subject's skin covering a body part, which selected area serves as a measurement site for measuring changes in the pulsatile arterial blood volume thereat, comprising:

a base for application to the selected area of the subject's skin at said measurement site;

a pressure applicator carried by said base for applying a static pressure to the subject's skin at said measurement site when said base is applied thereto;

and a sensor carried by said pressure applicator for sensing changes in the pulsatile arterial blood volume at said measurement site when the base is applied thereto;

said pressure applicator being designed to apply to said measurement site, when the base is applied thereto, a static pressure of a sufficient magnitude to partially unload the wall tension of, but not to occlude, the arteries at said measurement site;

said pressure applicator being configured to substantially prevent venous distention and blood pooling at said measurement site by applying sufficient external counter pressure to effectively collapse the underlying veins and limit the local venous blood flow to the arterial throughput while permitting free venous drainage with respect to said measurement site through tissues surrounding said measurement site;

said probe being configured to be applied to a relatively restricted area of the subject's skin, to apply said static pressure to said relatively restricted area, which area does not completely encircle the body part at said measurement site;

said pressure applicator occupying a relatively small fraction of the surface perimeter of the respective body part at said measurement site, to thereby permit free venous drainage from said measurement site via a wide region of unrestricted passageways surrounding the measurement site;

in combination with a clamping device for applying a clamping force to said base of the probe when applied to said measurement site, and a counterforce to the respective body part of the subject at the opposite side of said measurement site.

12. Apparatus for detecting and indicating a medical condition or a change in physiological state of a subject, comprising:
a probe according to claim 4, for application to a measurement site on the subject's skin and for producing an output corresponding to measured changes in the pulsatile arterial blood volume thereat;
and a data processor system for utilizing said measured changes to detect and indicate a medical condition or change in physiological state of the subject.

13. The apparatus according to claim 12, wherein said data processor system utilizes said measured changes in pulsatile arterial volume to indicate the peripheral arterial tone of the subject.

14. The apparatus according to claim 12, wherein said data processor system utilizes said measured changes in pulsatile arterial volume to indicate changes in the systemic blood pressure of the subject.

15. The apparatus according to claim 12, wherein said data processor system utilizes said measured changes to indicate the pulse rate of the subject.

16. The apparatus according to claim 12, wherein said data processor system utilizes said measured changes in the pulsatile arterial blood volume to indicate the level of vascular tone at the measurement site.

17. The apparatus according to claim 12, wherein said sensor is an optical sensor, and said data processor system utilizes said measured changes in pulsatile arterial volume to produce a measurement of the oxygen saturation level of the blood.

18. The apparatus according to claim 12, wherein said apparatus further comprises at least one additional probe according to claim 4, for application to at least one additional measurement site on the subject's skin and for measuring changes in the pulsatile arterial blood volume thereat; said data processor system utilizing the measured changes of both of said probes for detecting and indicating the medical condition or the change in physiological state of the subject.

19. The apparatus according to claim 18, wherein said probes are constructed for application to measurement sites in which the vascular beds thereat have different levels of autonomic nervous system activity or responsiveness.

20. The apparatus according to claim 18, wherein said probes are constructed for application to measurement sites in which the vascular beds thereat are mainly comprised of conduit (conducting) arteries and microcirculatory vascular beds respectively.

21. The apparatus according to claim 18, wherein said probes are constructed for application to measurement sites in which the pulsatile volume of the vascular beds are respectively predominantly affected by autonomic nervous system activity or by the level of systemic blood pressure.

22. The apparatus according to claim 18, wherein said probes are constructed for application to measurement sites in which the pulsatile volume of the vascular beds are respectively predominantly affected by autonomic nervous system activity or by the level of systemic blood pressure wherein said data processor system compares the outputs of said probes to indicate the medical condition or change in physiological state of the subject.

23. The apparatus according to claim 18, wherein said probes are constructed for application to measurement sites in which the pulsatile volume of the vascular beds are unequally affected by autonomic nervous system activity; and wherein said data processor compares the outputs of said probes to indicate the medical condition or change in physiological state of the subject.

24. The apparatus according to claim 18, wherein said probes are constructed for application to two or more measurement sites at a known distance from each other; and wherein said data processor system utilizes the outputs of said probes for indicating the pulse propagation velocity.

25. The apparatus according to claim 18, wherein at least one of said probes includes an electrode for sensing the electrocardiograph (ECG) signal of a subject;
and wherein said data processor system utilizes said measured changes in the pulsatile arterial blood volume, and said ECG signal, to determine the pulse transit time and/or pulse propagation velocity.

26. A method of detecting and indicating a medical condition or change in physiological state of a subject, comprising:
applying a probe according to claim 4 to a measurement site on the subject's skin for measuring changes in the pulsatile arterial blood volume thereat;
and utilizing said measured changes to detect and indicate a medical condition or change in physiological state of the subjects;
wherein said probe is applied to arterio-venous shunt rich palmar surfaces of the hand or plantar surfaces of the foot.

27. The method according to claim 26, wherein said probe is applied to a relatively restricted area of the subject's skin substantially overlying a medium to large sized artery.

28. A method of detecting and indicating a medical condition or change in physiological state of a subject, comprising:
applying a probe according to claim 4 to a measurement site on the subject's skin for measuring changes in the pulsatile arterial blood volume thereat;
and utilizing said measured changes to detect and indicate a medical condition or change in physiological state of the subject;
wherein said probe is applied to a relatively restricted area of the subject's skin substantially overlying a medium to large sized artery.

29. A method of detecting and indicating a medical condition or change in physiological state of a subject, comprising:
applying a probe according to claim 4 to a measurement site on the subject's skin for measuring changes in the pulsatile arterial blood volume thereat;
and utilizing said measured changes to detect and indicate a medical condition or change in physiological state of the subject;
wherein said probe is applied over a superficial artery for evaluating an endothelial function of the subject.

30. A method of detecting and indicating a medical condition or change in physiological state of a subject, comprising:
applying a probe according to claim 4 to a measurement site on the subject's skin for measuring changes in the pulsatile arterial blood volume thereat;
and utilizing said measured changes to detect and indicate a medical condition or change in physiological state of the subject;
wherein said probe is applied over a skin region predominantly containing microvascular blood vessels for evaluating an endothelial function of the subject.

31. A method of detecting and indicating a medical condition or change in physiological state of a subject, comprising:
applying a probe according to claim 4 to a measurement site on the subject's skin for measuring changes in the pulsatile arterial blood volume thereat;
and utilizing said measured changes to detect and indicate a medical condition or change in physiological state of the subject;
wherein at least one additional probe is applied to at least an additional measurement site on the subject's skin for measuring the pulsatile arterial blood volume thereat, the measurement of the additional probe(s) at the additional measurement site(s) also being utilized for detecting and indicating the medical condition or change in physiological state of the subject;
and wherein said probes are applied to measurement sites in which the vascular beds thereat have different levels of reactivity to autonomic stimulation.

32. The method according to claim 31, wherein said probes are applied to measurement sites in which the vascular beds thereof have different responses to reflex eliciting events.

33. The method according to claim 31, wherein at least two of said probes respectively include an electrode for sensing the electrocardiograph (EGG) signal of the subject, and wherein said probes are applied to measurement sites at a known distance from each other and the measured changes of said probes are utilized for indicating the pulse transit time and the pulse propagation velocity.

34. The method according to claim 31, wherein one of said probes is applied to a subject's body surface overlying a superficial conducting artery, and another of said probes is applied to a subject's body surface overlying a predominantly microcirculatory vascular bed.

35. The probe of claim 4, wherein a multiplicity of different sensors are used for sensing changes in the pulsatile arterial blood volume at said measurement site.

36. The method according to claim 26, wherein said probe is applied over a skin region predominantly containing microvascular blood vessels for deriving a signal for biofeedback input.

37. The method according to claim 26, wherein said probe is applied over a skin region overlying a superficial conducting artery for deriving a signal for biofeedback input.

38. The method according to claim 26, wherein said probe is applied over a skin region predominantly containing microvascular blood vessels for deriving a signal in response to a physical, pharmacological agent or mental stressor.

39. The method according to claim 26, wherein said probe is applied over a skin region overlying a superficial conducting artery for deriving a signal in response to a physical, pharmacological agent or mental stressor or stimulus.

40. The method recited in claim 26, wherein said detecting comprises viewing time-course of a peripheral arterial tone signal.

41. The method recited in claim 26, wherein said detecting comprises viewing variations in a peripheral arterial tone signal.

42. The method of claim 31, wherein a multiplicity of different sensors are used for detecting changes in the pulsatile arterial blood volume at said measurement sites.

43. The method of claim 31, wherein detecting of changes in the pulsatile arterial blood volume at said measurement sites is performed for deriving a signal for biofeedback input.

44. The method of claim 31, wherein detecting of changes in the pulsatile arterial blood volume at said measurement sites is performed for deriving a signal in response to a physical, pharmacological agent or mental stressor or stimulus.

45. The method of claim 31, wherein detecting changes in the pulsatile arterial blood volume at said measurement sites comprises viewing time-course of a peripheral arterial tone signal.

46. The method of claim 31, wherein detecting changes in the pulsatile arterial blood volume at said measurement sites comprises viewing variations in a peripheral arterial tone signal.

47. The probe according to claim 4, wherein pressure applied by said pressure applicator extends in area beyond the region of said sensor to extend the effective boundary of the pressure field overlying the sensing region, to substantially prevent venous distention and blood pooling at said measurement site and extended effective boundary of the pressure field by applying sufficient external counter pressure to effectively collapse the underlying veins and limit the local venous blood flow to the arterial throughput while permitting free venous drainage with respect to said measurement site through tissues surrounding said measurement site.

48. The apparatus according to claim 12, further including a sleep/wake detector, wherein said data processor system utilizes said measured changes to indicate the sleep/wake status of the subject.

49. The probe according to claim 3, wherein said pressure applicator is adapted to apply to said measurement site a static pressure which is above the subject's local venous pressure and slightly below the subject's diastolic blood pressure.

50. The probe according to claim 4, wherein said pressure applicator is adapted to apply to said measurement site a static pressure which is above the subject's local venous pressure and slightly below the subject's diastolic blood pressure.

51. The probe according to claim 11, wherein said pressure applicator is adapted to apply to said measurement site a static pressure which is above the subject's local venous pressure and slightly below the subject's diastolic blood pressure.

52. The probe according to claim 3, wherein said base is of a relatively non-stretchable material and carries said pressure applicator and sensor at the center thereof.

53. The probe according to claim 4, wherein said base is of a relatively non-stretchable material and carries said pressure applicator and sensor at the center thereof.

54. The probe according to claim 11, wherein said base is of a relatively non-stretchable material and carries said pressure applicator and sensor at the center thereof.

* * * * *